United States Patent [19]

Eibl et al.

[11] 4,159,988

[45] Jul. 3, 1979

[54] SYNTHETIC PHOSPHOLIPIDS, A PROCESS FOR THEIR MANUFACTURE AND THEIR USE

[75] Inventors: Hansjörg Eibl, Bovenden; Walter Diembeck, Göttingen; Stephen Kovatchev, Göttingen-Roringen, all of Fed. Rep. of Germany

[73] Assignee: Max-Planck-Gesellschaft zur Förderung der Wissenschaften e.V., Göttingen, Fed. Rep. of Germany

[21] Appl. No.: 870,326

[22] Filed: Jan. 18, 1978

Related U.S. Application Data

[63] Continuation of Ser. No. 602,181, Aug. 5, 1975, abandoned.

[30] Foreign Application Priority Data

Aug. 6, 1974 [DE] Fed. Rep. of Germany ....... 2437832

[51] Int. Cl.$^2$ .................. C07D 317/00; A23J 7/00; C07F 9/02; C11C 3/00
[52] U.S. Cl. .................. 260/340.9 R; 260/925; 260/945; 260/973; 260/403
[58] Field of Search ............... 260/403, 924, 945, 973, 260/978, 925, 340.9 R

[56] References Cited

U.S. PATENT DOCUMENTS

| | | | |
|---|---|---|---|
| 3,328,492 | 6/1967 | Gleason et al. | 260/924 |
| 3,577,446 | 4/1971 | Rakhit | 260/403 |
| 3,705,213 | 12/1972 | Pfeiffer et al. | 260/403 X |

*Primary Examiner*—John Niebling
*Attorney, Agent, or Firm*—Curtis, Morris & Safford

[57] ABSTRACT

Synthetic phospholipids having a varying phosphorus-nitrogen distance and a process for their manufacture are disclosed.

9 Claims, No Drawings

SYNTHETIC PHOSPHOLIPIDS, A PROCESS FOR THEIR MANUFACTURE AND THEIR USE

This is a continuation of application Ser. No. 602,181, filed Aug. 5, 1975 now abandoned.

The present invention relates to synthetic phospholipids and to a process for their manufacture and their use.

The process of the invention comprises the manufacture of synthetic phospholipids which do not occur in nature and have a varied phosphorus-nitrogen distance.

Naturally occurring phospholipids are fat-like triglycerides containing two long-chained fatty acids and a phosphoric acid radical to which a base is linked. They occur in all animal and vegetable cells, especially in the brain, heart, liver, egg yolk, as well as in soybeans. The most important ones among the naturally occurring phospholipids are the cephalins and lecithins, in which colamine or quoline are present as bases.

Lecithins and cephalins are widely used since they have colloidal, surface-active, emulsifying, softening, anti-oxidizing, purifying and physiological properties. Being natural products they are physiologically acceptable in foodstuffs and therefore superior to many synthetic substances of similar activity. They are added to margarine in order to assure a better linkage to water; when lecithin is used in chocolate and coating masses it brings about a better and quicker wetting of the mixing constituents, a reduction of viscosity and thus a considerable saving of expensive cacao butter. At the same time, rancidity and "fat-bloom" are prevented during storage. Lecithin when used in sweets helps to emulsify sirup with fat. At the same time, it prevents the fat from getting rancid and sugar from crystallizing. Bakery goods can be more readily processed owing to the improved wetting during the mixing operation. Up to 20% of the otherwise required fat can thus be saved, and the yield can be increased up to 2% owing to the better linkage to water.

Large amounts of soybean lecithin are also added to fodder material since this promotes the absorption of the foodstuffs in the digestive tube and taken together with fish- and meat-flour it counteracts the damaging effect of cholesterol.

Used for cosmetic purposes and in the manufacture of soap, small additions thereof improve the suppleness and absorption of ointments, creams, tooth pastes, soaps and the like.

In the leather and textile industries, lecithin emulsions are being used as adjuvants in the processing owing to their antioxidizing effect. In paints, lecithin prevents the pigments from settling and reduces the viscosity, thus improving the processing conditions. It is also possible to improve printing pastes and inks for paper and textiles using lecithin. Lecithin emulsions are also used in pesticides since these have a good stability and adhesiveness.

Lecithins and cephalins have recently gained a particular importance since it was founded out that they exercise important functions on celloxidation and other cellular processes. The function of the phospholipids in the cellular metabolism has, however, been little elucidated and is therefore particularly difficult since the isolated compounds are obtained in only small amounts and their syntheses involve great difficulties. The syntheses of phospholipids often require many steps, and the desired products are obtained in only small yields (cf. A. J. Slotboom and P. P. M. Bonsen, Chem. Phys. Liquids Page 301(1970).

Lecithin and cephalin are obtained from natural products, for example from egg yolk, cerebral matter, spinal marrow and soybeans. The commercial products have very much differing properties, and it is therefore difficult in many cases to use lecithin and cephalin for various applications owing to the differing content of phospholipids.

It is an object of this invention to provide a process for the synthesis of phospholipids which is simple and easy to manage without requiring the use of expensive starting materials. A further object of this invention is to provide new compounds which have a structure similar to the naturally occurring phospholipids and possess similar or even better properties than the naturally occurring phospholipids owing to the combination of lipophilic and hydrophilic as well as acidic and basic groups in the same molecule.

The process for the manufacture of synthetic phospholipids comprises

A. reacting a polyhydroxy compound having a free hydroxy group and the other hydroxy groups of which are protected with an ω-halogenalkyl-phosphoric acid dichloride of the general formula

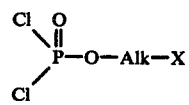

in which X stands for fluorine, chlorine, bromine or iodine, and Alk stands for an alkyl or cycloalkyl group having at least 3 C-atoms, and B. reacting the resulting reaction product with an amine of the formula

in which $R_1$, $R_2$ and $R_3$ each stands for hydrogen or methyl.

The present invention moreover relates to the synthetic phospholipids prepared according to the new process and to the use of the new compounds as stabilizers for enzyme compositions and as emulsifiers and as drugs.

The compounds prepared according to the invention may be used for the same purposes as the natural phospholipids.

The compounds of the invention have valuable pharmacological properties. The compounds which are analogous to lecithin are potent surfactants and as such have a great influence on natural cell membranes and on the permeability conditions in biomembranes. By selectively varying the phosphatetrimethylammonium distance of the fatty acid used and selectively varying the base used, the properties of the cell membranes can be modified in a selective manner.

When the surface activity of the cell membranes is influenced by means of the compounds of the invention, the activity of pharmaceutical compositions is modified as well, i.e. their absorbability and their distribution in the organism.

Owing to their marked surface activity, the compounds of the invention cause a change in the properties of cell membranes when administered to warm-blooded animals by the oral or intraperitoneal route. When administered in even higher concentrations, cytolytical phenomena are observed. The administration of sublytical doses causes changes in the cellular membranes.

Compounds having saturated fatty acid esters of 16 and more carbon atoms, for example palmitic acid, are immunological adjuvants, while compounds having chain lengths of less than 14 carbon atoms were found to cause an inhibition (imuno-suppressant action) of the imuno-apparatus. These results were observed with phosphoric acid quinoline esters. The immunological adjuvant effect reveals itselfs in a general increase in the antibody level.

The comprehensive variants of structure which were brought about on the lysophospholipid molecule led to more efficient adjuvants.

Enzymes in the cellular membranes which are dependent on phospholipids contain natural phospholipid mixtures having a large number of unsaturated fatty acids. Due to the instability of unsaturated fatty acids in the presence of oxygen, the stabilisation of such enzyme compositions is difficult.

Enzyme compositions of this kind, however, may be delipidized, thus losing their enzymatic activity. A reactivation of the enzyme can be obtained using the phospholipids of the invention having no unsaturated fatty acid radicals. Reactivation may be brought about by mixing the phospholipid in an adequate ratio with the compound of the invention. It is thus possible to reactivate and stabilize enzymes which depend on phospholipids. According to the concept of various authors, hybrid-formation and the cell fusions are induced by lysolecithin. Thus it is possible to produce cellhybrids in a similar manner as with Sendai virus. A disadvantage is the great cytolytic activity of the lysolecithins obtained from egg lecithin which are used for these investigations. The compounds of this invention having a finely varying cytolytic activity allow the experiments of cell fusion to be optimized, that is the cytolysis can be avoided.

As already mentioned above, the compounds of the invention are good emulsifiers owing to the combination of lipophilic and hydrophilic as well as of acidic and basic groups in the same molecule, and they form stable emulsions at a pH ranging from 0 to 11. They may therefore advantageously be used in detergents. In addition they have the further advantage that, owing to their close relation to natural phospholipids, they can be degraded in a biological manner, thus avoiding ecological problems. Moreover, the compounds of the invention having more than 6 carbon atoms between the phosphorus and the nitrogen atoms were found to be safe against the attack of phospholipases C and D, so that their bactericidal and bacteriostatic activities cannot be destroyed by these enzymes produced in cells.

According to the process of the present invention polyhydroxy compounds having a free hydroxy group are reacted with a halogenalkylphosphoric acid dichloride. The protection of the hydroxy groups in the polyhydroxy compound may be effected by etherification, esterification or ketalization. For the process of the invention, 1,2- or 1,3-diglycerides and other glycerol derivatives, and polyhydric aliphatic alcohols, such as erythritol, pentitols and hexitols, may generally be used as the polyhydroxy compounds. Examples of polyhydroxy compounds which may be reacted according to the invention are illustrated in detail later on in connection with the compounds of the invention.

The polyhydroxy compounds are reacted with a halogen-alkylphosphoric acid dichloride of the general formula

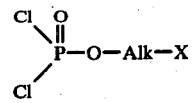

in which X stands for fluorine, chlorine, bromine or iodine, and Alk stands for an alkyl or cycloalkyl group having at least 3 C-atoms. Preferably ω-bromoalkylphosphoric acid dichlorides are used. In the above formula, Alk preferably contains 3 to 25 C-atoms, more preferably 3 to 16, and most preferably 3 to 12 C-atoms, in the case of alkyl groups, or 6 C-atoms in the case of cycloalkyl groups (cyclohexyl). The halogenalkylphosphoric acid dichlorides of the desired chain length are obtained by reacting halogenated alcohols of the following formula

of a corresponding chain length, that is Alk has the same meaning as given above, with phosphorus oxytrichloride. The said halogenated alcohols may be obtained from the corresponding ions. For example the brominated alcohols may be prepared by introducing a bromine atom per molecule of diol according to a simple process. The reaction product having one bromine atom is removed from the reaction medium by extraction and thus further bromination is excluded.

The reaction of halogenalkylphosphoric acid dichloride with the polyhydroxy compound is preferably carried out in an inert organic solvent, for example halogenated hydrocarbons such as chloroform, carbon tetrachloride, benzene, toluene, petroleum ether and the like. The reaction should be carried out with exclusion of moisture. The reaction temperature generally ranges from −10° to 50° C., preferably from 0° to 20° C. The reaction is preferably carried out in the presence of an inert base, for example triethylamine or pyridine. The halogenalkylphosphoric acid dichloride is generally dissolved in the inert solvent, and the base is added. While stirring, the polyhydroxy compound, likewise dissolved in an inert solvent, is added dropwise to the phosphorylation agent, where required while cooling.

Under these conditions, the reaction is smooth. It is generally complete within a short time. However, it is recommendable to continue stirring for some time to assure complete reaction. Reaction periods ranging from half an hour to five hours are usual.

The reaction may be checked, for example, by thin-layer chromatography. When the reaction is complete, the solvent and excess base are eliminated at a low temperature, and the reaction product may be separated by usual methods, for example by extraction. It is generally not necessary to purify the reaction product but it may be reacted immediately with the desired amine base without further purification.

For this purpose, the reaction product is dissolved in a suitable solvent, and an ethanolic or an aqueous solution in the corresponding amine base is added thereto. This reaction is carried out at room temperature or at a slightly elevated temperature, for example at 55° C., for 5 to 20 hours, or for 1 to 6 hours. The reaction procedure can be controlled by thin-layer chromatography.

Care should be taken that the necessary reaction time be not exceeded since, after the reaction is complete, the reaction product decomposes.

After it has been made sure that the reaction is complete, the reaction product is isolated in a known manner, for example it may be purified by column chromatography.

The yields of the products which are analytically pure, generally, range from 10 to 25% of the theoretical yield, calculated on the diglycerides used or on the other corresponding starting materials.

Examples of compounds which may be prepared according to the process of the invention are given in the following:

1. Lecithins and cephalins of the following formulae

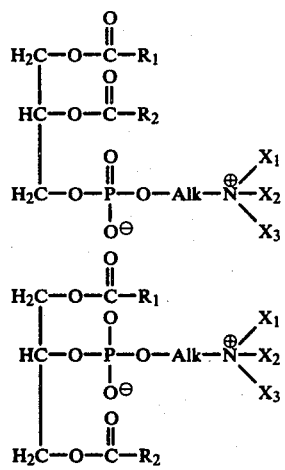

Starting materials are racemic or optically active 1,2- or 1,3-diglycerides having unsaturated, saturated or branched fatty acids or fatty acids containing a cycloalkane or an aromatic ring.

In the above formula, $X_1$, $X_2$ and $X_3$, independently of one another, each stand for a hydrogen atom or a methyl group, Alk is defined as above, $R_1$ and $R_2$ each stand for a straight-chain or branched saturated or unsaturated alkyl group which may be substituted by a cycloalkyl group or an aromatic group. The alkyl groups contain from 9 to 25 C-atoms, preferably 12 to 18 C-atoms, and most preferably 14 to 18 C-atoms. The cycloalkyl groups may contain from 5 to 7, preferably 5 to 6, C-atoms. As aromatic groups, for example phenyl groups or substituted phenyl groups may be mentioned. $R_1$ and $R_2$ may preferably stand for fatty acid radicals, for example radicals of palmitic acid, and stearic acid.

2. Lyso compounds of compounds of the general formula IV or V

Starting materials for the manufacture of the lyso compounds of the general formula IV or V are, for example, 1-acyl-2-benzylglyceral or 1-benzyl-2-acyl-glycerol. The starting materials may also be prepared biochemically from lecithins and cephalins by enzymatic splitting with phospholipases A 1 and A 2.

3. Analogs with Sugar alcohols

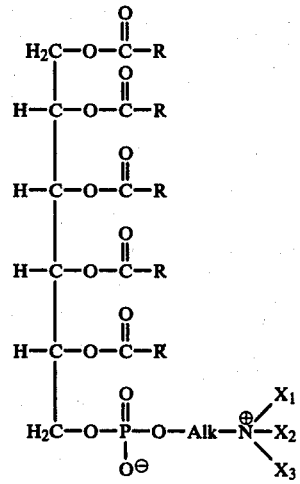

in which Alk, $X_1$, $X_2$ and $X_3$ are defined as above, and R has the same meaning as given for $R_1$ and $R_2$. The starting materials used are acylated saccharic alcohols containing z-1 acyl radicals in the case of z hydroxy groups, z being an integer of from 2 to 7. preferably 3 to 6, most preferably 4, 5 or 6. Cyclic sugar alcohols may also be used.

4. Ether analogs and ether-ester analogs of the compounds of Groups 1 to 3

For example

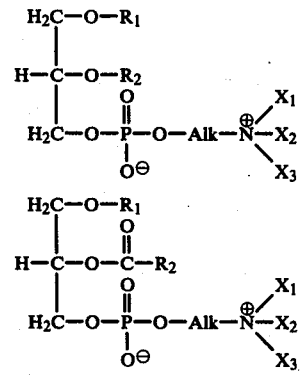

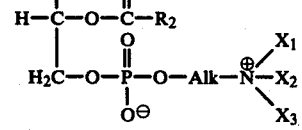

in which $R_1$, $R_2$, Alk, $X_1$, $X_2$ and $X_3$ are defined as further above.

Starting materials are the 1,2- and 1,3-dialkylglycerol ethers or ethyl glycerol alkyl ethers.

5. Dialkyl ketone glycerol phospholipids

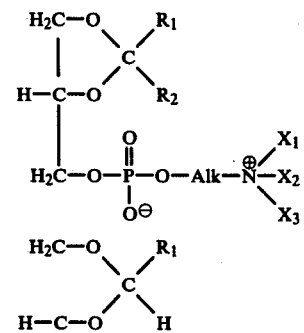

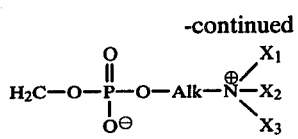

X

In the above formula IX and X, $R_1$, $R_2$, Alk, $X_1$, $X_2$ and $X_3$ are defined as above.

Starting substances are 1,2- and 1,3-dialkylketoneglycerols or the corresponding acetals which may be obtained from glycerol or 2-benzylglycerol by a reaction with the corresponding ketone or aldehyde. The ketone or aldehyde may also contain a cycloalkane or aromatic ring in the lateral chain.

6. Cycloalkyl ketone glycerol phospholipids

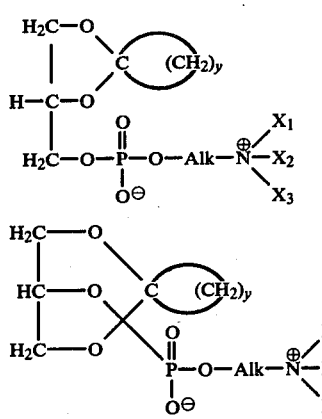

XI

XII

In the above formula XI and XII, Alk, $X_1$, $X_2$ and $X_3$ are defined as above, y stands for an integer of from 5 to 32, preferably 5 to 18, more preferably from 5 to 16, most preferably from 5 to 12, i.e. 5, 6, 7, 8, 9, 10, 11, 12, and so on. In the above formula, Alk may also contain 2 carbon atoms.

Starting substances are 1,2- and 1,3-cycloalkyl ketone glycerols which may be obtained from glycerol or 2-benzyl glycerol by a reaction with the corresponding cycloalkanone.

7. Desoxy lysolecithins and cephalins

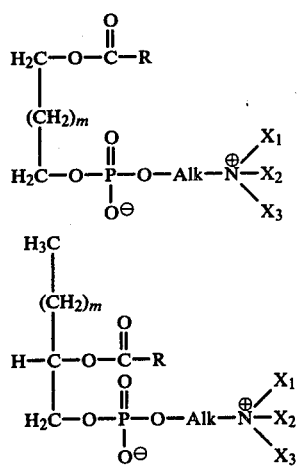

VIII

XIV

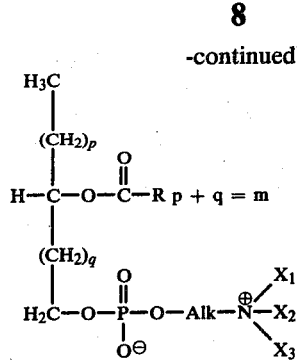

XV

In the above formulae, Alk, $X_1$, $X_2$, $X_3$, R are defined as above, m stands for zero or for an integer of from 1 to 14, preferably 1 to 8, most preferably for 2, 3, 4, 5 or 6. The sum of p and q makes up m.

Starting substances for the compounds of the general formula XIII, XIV and XV are the corresponding monoacyl alkane diols, preferably ω,ω'-monoacyl alkane diols. The alkane diols may be saturated, unsaturated or branched and may also contain a cycloalkane or an aromatic ring.

8. Ether analogs of the compounds of Group 7

The above classes of compounds are examples of compounds obtained according to the process of the invention. The process of the invention is generally applicable and may be used for the synthesis of many compounds. The compounds obtained according to the process of the invention may be isolated generally by column chromatography on silica gel. The analytically pure products are white, amorphous powders having an uncharacteristical melting point. Therefore, characterization is generally made by thin-layer chromatography and elementary analysis.

The following examples illustrate the invention.

EXAMPLE 1:

Preparation of brominated alcohols of different chain lengths according to a simplified method:

The compounds of the following type were synthesized:

Alk having 4 to 10 carbon atoms, i.e. n is an integer of 4 to 10.

Starting products were diols of the corresponding chain length having terminal alcohol functions. Since in each case, only one bromine atom per diol molecule was to be introduced, a process had to be found whereby the reaction product was eliminated immediately from the reaction medium and thus further reaction was excluded. For this purpose, an extraction method was suitable.

Diol and hydrobromic acid were placed in a round flask. The starting products were overlaid with petroleum benzine or with benzene/petroleum benzine. The selection of the extraction agent depended on the insolubility of the diol and the good solubility of the reaction product therein. The round flask was equipped with a reflux condenser. While very vigorously stirring by means of a magnetically operated stirrer, the mixture was refluxed by means of an adequate heating device until the reaction of the starting product was complete. The proceeding reaction was checked by means of thin-layer chromatography.

The extraction medium phase was then separated and dried with calcium sulfate. After the siccative had been filtered off, the extraction medium was eliminated in the rotary evaporator. The residue was subjected to fractionated distillation in an oil pump vacuum.

The yield ranged from about 80 to 95 percent of the theoretical yield, calculated on the diol used. 4-Bromobutanol-(1) and 5-bromo-pentanol-(1) were prepared as follows:

22.5 g (0.25 mol) of 1,4-butane diol or
26 g of 1,5-pentane diol (0.025 mol)

were refluxed together with 80 g of hydrobromic acid (47 percent strength, 0.48 mol),
500 ml of benzene and
50 ml of petroleum benzine (boiling point 100 to 140° C.)

for 6.5 and 6 hours, respectively.

The rest of the brominated alcohols were prepared as follows:

29.6 g (0.25 mol) of the corresponding diol were refluxed together with
80 g (0.48 mol) of hydrobromic acid (47 percent strength),
1500 ml of petroleum benzine (boiling point 100° to 140° C.).

The following reaction products were prepared:

Table

| Reaction product | Reaction period | Physical constants |
|---|---|---|
| 4-bromobutanol-(1) | 6.5 hours | boiling point (0.7 mmHg) 58 – 60° C. |
| 5-bromopentanol-(1) | 6 hours | boiling point (0.5 mmHg) 72 – 74° C. |
| 6-bromohexanol-(1) | 1.5 hours | boiling point (0.6 mmHg) 85 – 87° C. |
| 7-bromoheptanol-(1) | 1.5 hours | boiling point (0.5 mmHg) 87 – 89° C. |
| 8-bromooctanol-(1) | 1 hour | boiling point (0.5 mmHg) 110 – 112° C. |
| 9-bromononanol-(1) | 1 hour | boiling point (0.4 mmHg) 112 – 114° C. |
| 10-bromodecanol-(1) | 30 minutes | boiling point (0.3 mmHg) 124 – 126° C. |

Up to the 8-bromooctanol-(1), the reaction products were colorless liquids. 9-bromononanol-(1) and 10-bromodecanol-(1) were white solid products at room temperature. Brominated alcohols of greater chain length may principally be prepared also according to this method. Since all these reaction products were solid substances, they were purified by recrystallization.

EXAMPLE 2

Preparation of lecithins having a modified phosphorus-nitrogen distance in the polar head:

A. ω-bromoalkylphosphoric acid dichloride 32 mmols = 30 ml of phosphorus oxytrichloride (freshly distilled, boiling point 105° to 107° C.) in 70 ml of absolute chloroform (distilled for 90 minutes with circulation over $P_2O_5$) were placed in a round flask. At room temperature, nitrogen was fed into this solution for a short time to expel air. The flask was equipped with a dropping funnel and sealed airtight. While stirring with a magnetically operated stirrer, 20 mmols of the brominated alcohol of desired chain length in 50 ml of absolute chloroform were slowly added dropwise at room temperature with the exclusion of moisture. Stirring was continued for about 12 hours. The hydrogen chloride resulting from the reaction as well as excess phosphorus oxytrichloride and chloroform were eliminated at 30° C. in a rotary evaporator. To eliminate any trace of phosphorus oxytrichloride, toluene was added and likewise drained off.

The conversion rate was 95 to 100%, and the reaction was checked by means of thin-layer chromatograms.

B. Phosphorylation

The ω-bromoalkylphosphoric acid dichloride obtained sub A. was taken up in 60 ml of absolute chloroform, and the solution was cooled to 0° C. While stirring by means of a magnetically operated stirrer, 10 ml of triethylamine (dried over lithium-aluminum-hydride and freshly distilled) were added. 14 mmols of the corresponding diglyceride, for example
SN-1,2-dipalmitoylglycerol,
SN-1,2-dimyristoylglycerol,
1,2-dipentadecylketoneglycerol
or another of the above-mentioned starting substances in 60 ml of absolute chloroform were slowly added dropwise at 30° to 35° C. while stirring by means of a magnetically operated stirrer and with the exclusion of atmospheric moisture.

It was made sure by thin-layer chromatography that the reaction was almost complete during the dropwise addition. During the reaction, the light yellow solution turned into a dark-brown colored solution. Stirring was continued for another 3 to 5 hours. Chloroform and triethylamine were then eliminated at 35° C. in a rotary evaporator. The reaction product was taken up in 100 ml of tetrahydrofuran. While stirring, 1M sodium acetate solution of pH 8.4 was added until the solution remained weakly alkaline. 100 ml of diisopropylether were then added to the reaction product thus hydrolyzed, and the mixture was stirred for 1 hour. After the phases had been separated, extraction was repeated using 50 ml of ether. The combined ether phases were stirred over sodium carbonate for 1 hour, filtered, and ether was then eliminated in the rotary evaporator.

The subsequent reactions were carried out without further purification of this reaction product.

C. Reaction with an amino base

The reaction product obtained sub B. was taken up in 150 ml of butanone for further reaction yielding lecithins. When a cephalin was to be prepared, it was dissolved in 50 ml of chloroform and in 100 ml of methanol. 100 ml of acetonitrile and 100 ml of an ethanolic or aqueous solution of the corresponding amino base were added thereto.

The reaction vessel was sealed airtight and maintained for 1 to 6 hours at 55° C., or for 5 to 20 hours at room temperature. The reaction procedure was checked by thin-layer chromatography. When the necessary reaction time was exceeded, the reaction product decomposed, which was manifested by a strong reduction in yield. The volatile constituents of the reaction mixture were then eliminated at 50° C. in a rotary evaporator. The residue was taken up in 150 ml of chloroform, 100 ml of 2% formic acid, and 200 ml of methanol were added, and the mixture was shaken. The reaction product was in the chloroform phase and was treated with 100 ml of 0.1M sodium acetate solution of pH 5.6 and 200 ml of methanol for neutralisation purposes. Upon repeated separation of the phases, the chloroform phase was dried over 10 g of sodiumsulfate and the chloroform was eliminated in the rotary evaporator.

The so-obtained crude product was purified by means of column chromatography. For this purpose, a column was charged with a suspension obtained for 100 g of silica gel (Mellinckrodt AR p. a.) in a solvent system of chloroform/methanol/ammonia = 200/15/1. The product dissolved in 10 to 15 ml of solvent was then applied to the top of this column, and contaminants were then eluted by means of the above-said system. The reaction product was then eluted with chloroform/methanol/ammonia = 65/15/1 and 65/30/3, respectively. The fractions were checked by thin-layer chromatography as to their purity.

The yields of the analytically pure products ranged from 10 to 25% of the theoretical yield, calculated on the diglycerides used or on other corresponding starting substances.

The compounds cited in the following with their individual analytical data were prepared:

Group 1

SN-1,2-dipalmitoylglycerol-3-phosphoric acid-5-trimethylaminopentylester $C_{43}H_{88}NO_9P$ mol weight: 794.15
calculated: C, 65.03%; H, 11.17%; N, 1.76%; P, 3.90%. found: C, 64.36%, H, 11.04%; N, 1.84; P, 3.91%.

Group 2:

SN-1-palmitoylglycerol-3-phosphoric acid-5-trimethylaminopentylester $C_{27}H_{58}NO_8P$ mol. weight: 537.72
calculated: C, 58.35%; H, 10.52%; N, 2.52%; P, 5.57%.

The analytical data obtained agreed with the calculated values.

Group 3:

1,2,3,4,5-pentamyristoyl-D-mannitol-6-phosphoric acid-7-trimethylaminoheptylester $C_{92}H_{166}NO_{14}P$ mol. weight: 1,541.31
calculated: C, 71.69%; H, 10.86%; N, 0.91%; P, 2.01%.

The analytical data obtained agreed with the calculated values.

Group 4:

a. 1-palmitoyl-2-hexadecyletherglycerol-3-phosphoric acid-9-trimethylaminononylester $C_{47}H_{98}NO_8P$ mol. weight: 836.27
calculated: C, 67.50%; H, 11.81%; N, 1.67%, P, 3.70%.

The analytical data obtained corresponded to the calculated values.

b. 1,3-dioctyletherglycerol-2-phosphoric acid-6-trimethylaminohexylester $C_{28}H_{62}NO_7P$ mol. weight: 555.78 calculated: C, 60.51%; H, 11.24%; N, 2.52%; P, 5.57%.

The analytical data obtained corresponded to the calculated values.

Group 5:

1,2-dipentadecylketoneglycerol-3-phosphoric acid-6-trimethylaminohexylester $C_{43}H_{90}NO_7P$ mol. weight: 750.12
calculated: C, 67.25%; H, 11.83%; N, 1.87%; P, 4.13%. found: C, 67.28%; H, 11.87%; N, 1.82%; P, 4.14%.

Group 7:

1-myristoylpropanediol-3-phosphoric acid-4-trimethylaminobutylester $C_{24}H_{52}NO_7P$ mol. weight: 497.65
calculated: C, 57.92%; H, 10.53%; N, 2.81%; P, 6.22%.

The analytical data obtained corresponded to the calculated values.

Group 8:

1-tetradecyletherpropanediol-3-phosphoric acid-4-trimethylaminobutylester $C_{24}H_{54}NO_6P$ mol. weight: 483.67
calculated: C, 59.60%; H, 11.25%; N, 2.90%; P, 6.40%.

The analytical data obtained corresponded to the calculated values.

Group 1:

SN-1,2-dipalmitoylglycerol-3-phosphoric acid-6-trimethylaminohexylester, mol. weight: 808.18

$C_{44}H_{90}NO_9P$ calculated: C, 65.39%; H, 11.23%; N, 1.73%; P, 3.83%. found: C, 66.66%; H, 11.45%; N, 1.80%; P, 4.08%.

SN-1,2-dipalmitoylglycerol-3-phosphoric acid-7-trimethylaminoheptylester, mol. weight: 822.20

$C_{45}H_{92}NO_9P$ calculated: C, 65.74%; H, 11.28%; N, 1.70%; P, 3.77%. found: C, 64.90%; H, 11.16%; N, 2.02%; P, 4.59%.

SN-1,2-dipalmitoylglycerol-3-phosphoric acid-8-trimethylaminooctylester, mol. weight: 836.23

$C_{46}H_{94}NO_9P$ calculated: C, 66.07%; H, 11.33%; N, 1.68%; P, 3.70%. found: C, 64.15%; H, 10.91%; N, 2.30%; P, 4.60%.

SN-1,2-dipalmitoylglycerol-3-phosphoric acid-9-trimethylaminononylester, mol. weight: 850.26

$C_{47}H_{96}NO_9P$ calculated: C, 66.39%; H, 11.38%; N, 1.65%; P, 3.64%. found: C, 66.28%; H, 11.43%; N, 1.85%; P, 3.85%.

Group 5:

1,2-dipentadecylkentoneglycerol-3-phosphoric acid-5-trimethylaminopentylester, mol. weight: 736.11

$C_{42}H_{83}NO_7P$ calculated: C, 66.90%; H, 11.78%; N, 1.90%; P, 4.21%. found: C, 67.06% H, 11.78% N, 2.06%, P, 4.22%

1,2-dipentadecylketoneglycerol-3-phosphoric acid-8-trimethylaminooctylester, mol. weight: 778.19

$C_{45}H_{94}NO_7P$ calculated: C, 67.91%; H, 11.92%; N, 1.80%; P, 3.98%. found: C, 68.21%; H, 11.93%; N, 1.89%; P, 3.95%.

We claim:

1. A synthetic phospholipid prepared by reacting an aliphatic or cycloaliphatic polyhydroxy compound having one free hydroxy group, the remaining hydroxy groups being protected, with an ω-haloalkylphosphoric acid dichloride of the formula

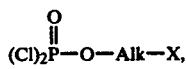

wherein X is fluorine, chlorine, bromine, or iodine, and then reacting the resulting reaction product with an amine of the formula

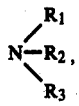

wherein $R_1$, $R_2$, and $R_3$ are each hydrogen or methyl, the improvement wherein Alk is alkyl or cycloalkyl having from 6 to 16 carbon atoms.

2. SN-1,2-dipalmitoylglycerol-3-phosphoric acid-5-trimethylaminopentylester.

3. SN-1-palmitoylglycerol-3-phosphoric acid-5-trimethylaminopentylester.

4. 1,2,3,4,5-pentamyristoyl-D-mannitol-6-phosphoric acid-7-trimethylaminoheptylester.

5. 1-pelmitoyl-2-hexadecyletherglycerol-3-phosphoric acid-9-trimethylaminononylester.

6. 1,3-diectyletherglycerol-2-phosphoric acid-6-trimethylaminohexylester.

7. 1,2-dipentadecylketoneglycerol-3-phosphoric acid-6-trimethylaminohexylester.

8. 1-myristoyl-propanediol-3-phosphoric acid-4-trimethylaminobutylester.

9. 1-tetradecyletherpropanediol-3-phosphoric acid-4-trimethylaminobutylester.

* * * * *